(12) United States Patent
Hampton et al.

(10) Patent No.: US 10,213,613 B2
(45) Date of Patent: Feb. 26, 2019

(54) SYSTEM AND METHOD FOR USING DIAGNOSTIC PULSES IN CONNECTION WITH DEFIBRILLATION THERAPY

(71) Applicant: Physio-Control, Inc., Redmond, WA (US)

(72) Inventors: David R. Hampton, Woodinville, WA (US); Isabelle Banville, Newcastle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 15/187,684

(22) Filed: Jun. 20, 2016

(65) Prior Publication Data

US 2016/0287890 A1    Oct. 6, 2016

Related U.S. Application Data

(63) Continuation of application No. 14/282,751, filed on May 20, 2014, now Pat. No. 9,370,665, which is a
(Continued)

(51) Int. Cl.
*A61N 1/39* (2006.01)
*A61N 1/38* (2006.01)
(Continued)

(52) U.S. Cl.
CPC ......... *A61N 1/3962* (2013.01); *A61H 31/005* (2013.01); *A61M 5/1723* (2013.01); *A61N 1/025* (2013.01); *A61N 1/385* (2013.01); *A61N 1/39* (2013.01); *A61N 1/3925* (2013.01); *A61N 1/3987* (2013.01); *A61H 2031/002* (2013.01); *A61M 2230/005* (2013.01); *A61M 2230/04* (2013.01)

(58) Field of Classification Search
CPC .................................... A61N 1/39; A61B 5/04
USPC ............................................... 607/5; 600/509
See application file for complete search history.

(56) References Cited

U.S. PATENT DOCUMENTS

5,318,591 A    6/1994   Causey et al.
5,978,703 A   11/1999   Kroll et al.
(Continued)

OTHER PUBLICATIONS

International Search Report for PCT/US2006/003348, dated May 5, 2006, 3 pages.

*Primary Examiner* — Carl H Layno
*Assistant Examiner* — Jon Eric C Morales
(74) *Attorney, Agent, or Firm* — Lane Powell PC (57) ABSTRACT

An external defibrillator system is disclosed that generates and applies a diagnostic signal to the patient in conjunction with defibrillation therapy. The diagnostic signal is designed to elicit a physiologic response from the patient's heart, namely, mechanical cardiac response and electrical cardiac response, electrical cardiac response only, or no cardiac response. Depending upon the type of cardiac response detected, the system selects an appropriate resuscitation protocol that considers the likely responsiveness of the patient to defibrillation therapy. In one practical embodiment, a stimulus signal is applied to patients that show mechanical and electrical capture in response to the diagnostic signal. The stimulus signal maintains the mechanical capture (and, therefore, perfusion) for a period of time prior to the delivery of a defibrillation pulse.

27 Claims, 3 Drawing Sheets

Related U.S. Application Data continuation of application No. 11/048,303, filed on Jan. 31, 2005, now Pat. No. 8,731,658.

(51) Int. Cl.
*A61H 31/00* (2006.01)
*A61M 5/172* (2006.01)
*A61N 1/02* (2006.01)

(56) References Cited

U.S. PATENT DOCUMENTS

| | | |
|---|---|---|
| 6,167,306 A | 12/2000 | Kroll et al. |
| 6,185,457 B1 | 2/2001 | Kroll et al. |
| 6,230,056 B1 | 5/2001 | Kroll |
| 6,298,267 B1 | 10/2001 | Rosborough et al. |
| 6,314,319 B1 | 11/2001 | Kroll et al. |
| 6,351,670 B1 | 2/2002 | Kroll |
| 6,560,484 B1 | 5/2003 | Kroll et al. |
| 6,567,697 B1 | 5/2003 | Kroll et al. |
| 8,731,658 B2 | 5/2014 | Hampton et al. |
| 2003/0060723 A1 | 3/2003 | Joo et al. |
| 2004/0049235 A1 | 3/2004 | Deno et al. |
| 2006/0229680 A1* | 10/2006 | Chapman .......... A61N 1/39 607/5 |
| 2007/0208263 A1* | 9/2007 | John .......... A61B 5/0452 600/509 |

* cited by examiner

SYSTEM AND METHOD FOR USING DIAGNOSTIC PULSES IN CONNECTION WITH DEFIBRILLATION THERAPY

RELATED APPLICATION DATA

This application is a continuation of U.S. patent application Ser. No. 14/282,751, is now U.S. Pat. No. 9,370,665, which is a continuation of granted U.S. Pat. No. 8,371,658, both of which are incorporated by reference herein for all purposes

TECHNICAL FIELD

The present invention relates generally to defibrillator systems. More particularly, the present invention relates to a defibrillator system that applies diagnostic electrical pulses to the patient during a resuscitation event to determine a recommended treatment protocol.

BACKGROUND

A normal human heart pumping pattern is called a sinus rhythm, and the pattern is regulated by the body's biological pacemaker within the upper right chamber of the heart, which is commonly referred to as the right atrium. This natural pacemaker, which is generally referred to as the sinoatrial ("SA") node, sends electrical signals to the right and left ventricular muscles in the lower chambers of the heart. The ventricular muscles then implement the pumping action under the control of the SA node. The right ventricular muscle pumps blood to the lungs for oxygenation, and the left ventricular muscle pumps the oxygenated blood to various parts of the body.

In certain circumstances, the normal or sinus heartbeat rhythm may be adversely affected as a result of some type of malfunction in the heart's electrical control system. When this type of malfunction occurs, an irregular heartbeat may result, causing the ventricular muscles to pump ineffectively, thus reducing the amount of blood pumped to the body. This irregular heartbeat is generally referred to as an arrhythmia.

A particularly serious arrhythmia is known as ventricular fibrillation ("VF"), which is a malfunction characterized by rapid, uncoordinated cardiac movements replacing the normal contractions of the ventricular muscles. In this event, the ventricular muscles are not able to pump blood out of the heart, and there is no initiation of a coordinated heartbeat, leading to death within minutes. VF rarely terminates spontaneously, and its unpredictability exacerbates the clinical problem of treating patients in sudden cardiac arrest. Physicians emphasize the critical importance of rapid therapeutic intervention to prevent the loss of life.

Defibrillators are devices for providing life-saving electrical therapy to persons experiencing an irregular heat beat, such as VF. A defibrillator provides an electrical stimulus to the heart in an attempt to convert the irregular heat beat to a normal sinus rhythm. One commonly used type of defibrillator is the external defibrillator, which sends electrical pulses to the patient's heart through external electrodes applied to the patient's chest. External defibrillators may be manually operated (as are typically used in hospitals by medical personnel), semi-automatic, semi-automated, fully automatic, or fully automated devices, allowing them to be used in any location where an unanticipated arrhythmic event may occur. In practice, defibrillation pulses are administered to the patient when necessary, either in the judgment of medical personnel or as recommended by automated interpretive algorithms ("Shock Advisory Systems"), and therapeutic protocols may further recommend that cardiopulmonary resuscitation ("CPR"), assisted ventilation, and/or supplemental drug therapies, among others, be administered between consecutive defibrillation pulses. CPR includes the delivery of chest compressions to the patient (to stimulate blood flow). Ventilation includes the delivery of air to the lungs by mechanical or physiologic means (e.g., mouth to mouth ventilation). Drugs may be delivered to stimulate cardiac tissue or to inactivate inhibiting or damaging substances in the heart, enhancing the effectiveness of defibrillator pulses.

The heart responds to defibrillation pulses in different ways depending upon how long the heart has been without perfusion. The prior art includes techniques that determine whether the heart is in a state that requires defibrillation therapy, and techniques that analyze the VF waveform to predict the responsiveness of the heart to defibrillation. These latter techniques are only able to make predictions based on statistical correlations between characteristics of the electrocardiogram ("ECG") signal and the probability of successful defibrillation in a population exhibiting similar measurements. As such, the predictions can be inaccurate and the results can be corrupted by artifact.

Accordingly, it is desirable to have a system for assessing the likelihood of defibrillation therapy success that addresses the shortcomings of prior art systems and methods. Furthermore, other desirable features and characteristics of the present invention will become apparent from the subsequent detailed description and the appended claims, taken in conjunction with the accompanying drawings and the foregoing technical field and background.

BRIEF SUMMARY

A system and method for determining effectiveness of defibrillation therapy for a patient utilizes a diagnostic signal before and/or after defibrillation. The diagnostic signal may include one or more electrical pulses designed to elicit a physiologic response from the patient, such as a detectable response from the patient's heart. Different therapy protocols can be recommended or initiated based upon the detected patient response. Thus, for some patients, time that might otherwise be spent performing analysis and defibrillation can instead be used to administer CPR, ventilation, and/or drugs which will enhance the patient's responsiveness to defibrillation therapy (in this context, a "responsive" patient resumes a perfusing rhythm after application of a defibrillation pulse, while an "unresponsive" patient exhibits continued VF or other non-perfusing cardiac rhythm, such as asystole, after application of a defibrillation pulse). In other patients, immediate defibrillation therapy might be the preferred resuscitation protocol to rapidly restore perfusion. A diagnostic technique according to the invention is quick, noninvasive, and simple to implement in existing defibrillation and/or monitoring devices, including internal devices. In addition, the diagnostic technique need not rely on retrospective indirect information from VF waveform analysis, knowledge of other patient factors, or statistical data.

In accordance with one aspect of the invention, a stimulus signal is applied to the patient if a diagnostic signal elicits mechanical and electrical cardiac response from the heart. The stimulus signal is designed to maintain mechanical capture (which causes perfusion) until defibrillation therapy is administered. The application of the stimulus signal is desirable to enhance the patient's responsiveness to the defibrillation therapy, and the stimulus signal can be employed in lieu of CPR.

The above and other aspects of the invention may be carried out in one form by a method for determining effectiveness of defibrillation therapy for a patient. The method involves applying a diagnostic signal to the patient, where the diagnostic signal has characteristics for eliciting a physiologic response from the patient, detecting, in response to the diagnostic signal, a current physiologic response from the patient, and identifying a resuscitation protocol based upon the current physiologic response. The identified resuscitation protocol considers a likely response by the patient to defibrillation therapy or to continued application of stimulus pulses.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely exemplary in nature and is not intended to limit the invention or the application and uses of the invention. For example, a practical embodiment of the invention may be deployed in connection with an automatic or automated external defibrillator, a semi-automatic or semi-automated external defibrillator, a manual external defibrillator, patient monitoring systems, and possibly implantable defibrillator devices. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of practical defibrillator systems and that the system described herein is merely one exemplary application for the invention.

For the sake of brevity, conventional techniques related to heart monitoring, detection of non-perfusing cardiac rhythms, estimation of the probability of defibrillation pulse success based on VF waveform characteristics, defibrillator device operation, the detection of electrical capture of the heart, the detection of mechanical capture of the heart, resuscitation techniques and protocols, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

The heart responds to externally applied electrical stimuli in different ways depending upon how long the heart has been without perfusion. For example, "pacing" pulses will usually elicit both electrical and mechanical capture in normal hearts or those experiencing only brief periods of fibrillation. On the other hand, hearts that have been without perfusion for longer periods (for example, eight minutes) will exhibit electrical cardiac response without a mechanical cardiac response. After long periods without perfusion, no electrical or mechanical cardiac response can be elicited. These findings can be used as the basis for a methodology to probe the state of the heart as described in more detail herein. Briefly, if a diagnostic signal is applied to the patient prior to a defibrillation pulse, then patients likely to respond to defibrillation therapy will react with certain detectable physiologic characteristics. Patients less likely to respond to defibrillation therapy will react with different detectable physiologic characteristics, while patients likely to be unresponsive to defibrillation therapy will not react to the diagnostic signal.

As mentioned above, a device configured in accordance with the invention detects, in response to a diagnostic signal applied to the patient, physiologic responses from the patient. As used herein, a "physiologic response" means a measurable or detectable reaction, condition, effect, or characteristic of the patient or any biological system of the patient, including, for example, a neurological response, a muscular response, a cardiac response, or the like. As used herein, a "cardiac response" means a measurable or detectable reaction, condition, effect, or characteristic of the cardiac system of the patient, including, for example, electrical cardiac response, mechanical cardiac response, or the like. Electrical capture is one particular type of electrical cardiac response, and mechanical capture is one particular type of mechanical cardiac response.

In contrast to prior art techniques, the resuscitation methodologies described herein utilize a diagnostic signal to test the patient's likely response to defibrillation electrotherapy. In patients who have short downtimes and healthy myocardium, a defibrillation pulse is the best possible therapy. In patients suffering longer periods without perfusion, successful cardioversion is less likely, and time that might otherwise be spent performing analysis and defibrillation can be better spent administering CPR or drugs to the patient. The resuscitation techniques described herein provide an effective means for determining an appropriate resuscitation protocol based upon the patient's detected physiologic response to the diagnostic signal. The outcome of a diagnostic signal as described herein can also be used to prescribe therapy or resuscitation protocols (e.g., CPR, drugs, additional defibrillation therapy, or the like) following a defibrillation pulse.

Furthermore, recent studies have shown that defibrillation success may be enhanced by preceding a defibrillation pulse with a period of coronary perfusion. This perfusion is ordinarily obtained by applying manual or mechanical chest compressions to squeeze blood from the heart and into the vasculature. Benefit is obtained by oxygenating the myocardium, restoring ionic balances, and removing toxic metabolic byproducts, all of which increase the likelihood of subsequent defibrillation success. Recent experimental observations suggest that hearts which have been without perfusion for less than four minutes will respond to certain electrical stimulus signals with both electrical cardiac response (e.g., electrical capture) and mechanical cardiac response (e.g., mechanical capture). Mechanical capture, in particular, leads to ejection of blood from the heart, and may substitute for chest compressions in situations where the patient has been without perfusion for only a short period of time. Electrical capture offers benefits by cycling the electrophysiologic mechanisms of the cell and restoring normal ionic distributions, which also increases the likelihood of successful defibrillation.

One example resuscitation technique described herein applies an external stimulus signal to the patient to stimulate the heart to increase cardiac output in bradycardia. Although long periods of cardiac arrest cause the heart to be unresponsive to external pacing, the heart remains responsive over short periods without perfusion. The externally applied stimulus signal stimulates cardiac output in these patients without the need for external chest compressions, and may provide lay rescuers (who often arrive on the scene within the first few minutes of an arrest) with an alternative to performing CPR. A practical embodiment of the invention can be implemented in an external defibrillator device by applying the stimulus signal via conventional defibrillation electrode pads.

Figure 1:
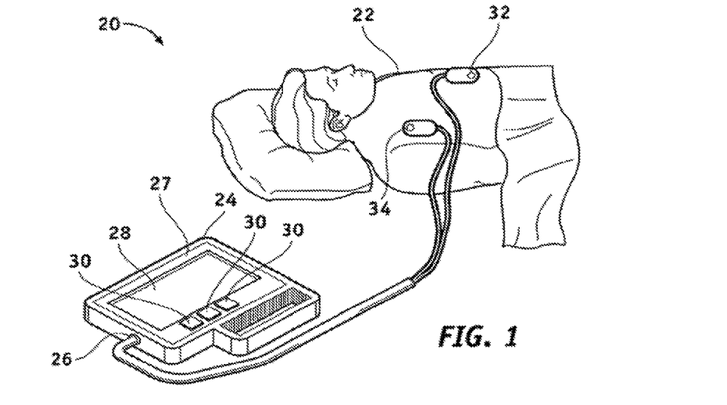
FIG. 1 is an illustration of an external defibrillator system connected to a patient.

FIG. 1 depicts a defibrillator system 20 that is configured to deliver defibrillation therapy to a patient 22, such as a victim of VF. The defibrillator system 20 includes, but is not limited to, an external defibrillator device 24 having a connection port 26 that is configured to receive one or more cables or wires corresponding to one or more patient electrodes 32/34. In practice, external defibrillator device 24 can be any number of external defibrillators, such as an automatic external defibrillator or automated external defibrillator ("AED"), a semi-automatic or semi-automated external defibrillator, or a manually operated external defibrillator. As used herein, an automatic or automated activity occurs without human intervention. As used herein, an "operator" of a defibrillator or monitoring system includes, without limitation: a caregiver; a rescuer; medical personnel; a clinician; or any person having manipulative access to the defibrillator or monitoring system. Unless otherwise indicated, these terms may be interchangeably used in the following description.

External defibrillator device 24 preferably includes a user interface 27 having a display 28 that is configured to visually present various measured or calculated parameters of patient 22 and/or other information to the operator (not shown) of external defibrillator device 24. For example, display 28 can be configured to visually present the transthoracic impedance, ECG, and/or other physiology signals of patient 22. User interface 27 can also include one or more input devices (e.g., switches or buttons) 30 that are configured to receive commands or information from the operator. External defibrillator device 24 is configured to generate a charge that is delivered to patient 22 as the defibrillation therapy pulse via electrodes 32/34.

Electrodes 32/34 are typically multifunction electrodes in that they are configured both to provide defibrillation therapy and to sense one or more physiology and/or physical parameters of the patient 22 that are received by external defibrillator device 24 at connection port 26. This is a typical configuration in an AED type device; it will be understood by those skilled in the art that electrodes may be designed differently for different machines. As described in more detail below, the signals provided by electrodes 32/34 may be analyzed by external defibrillator device 24 to detect electrical cardiac response of the heart, mechanical cardiac response of the heart, or both. In some practical embodiments, defibrillator system 20 may incorporate one or more additional sets of sensors that are specifically designed to monitor patient 22 for electrical capture and/or mechanical capture. Other defibrillators, including for example manual defibrillators, may also have an additional set of electrodes (not shown), in addition to the multifunction electrodes, used to receive ECG information. These additional electrodes, ECG electrodes, are generally smaller than therapeutic/multifunction electrodes, and ECG electrodes typically plug into a separate port (not shown) than the therapeutic/multifunction electrodes. As is understood in the art, ECG electrodes typically have a three wire lead, though other arrangements are possible. The signals provided by the one more electrodes 32/34 are preferably evaluated by the external defibrillator device 24 to determine, among other things, whether a defibrillation shock should be applied to patient 22 in accordance with techniques known to those of ordinary skill in the art. This external defibrillator device 24 can, in some embodiments, also evaluate the signals provided by the one more electrodes 32/34 to determine the waveform parameters of the defibrillation shock (e.g., sinusoidal, monophasic, biphasic, truncated) as well as magnitude and duration; AEDs often include a preprogrammed energy protocol. As is understood in the art, manual defibrillators may allow for a manual selection of shock parameters.

Although not depicted in FIG. 1, defibrillator system 20 may be deployed in conjunction with a separate patient monitoring device that is suitably configured to monitor the ECG of patient 22, administer diagnostic and stimulus signals to patient 22 (described in more detail below), analyze other physiology signals of patient 22, and/or monitor patient 22 for certain physiologic responses. The separate patient monitoring device may communicate with the caregiver or external defibrillator device 24 to facilitate the resuscitation techniques described herein. In other words, external defibrillator device 24 may be employed to administer defibrillation therapy under the control of the separate patient monitoring device.

Figure 2:
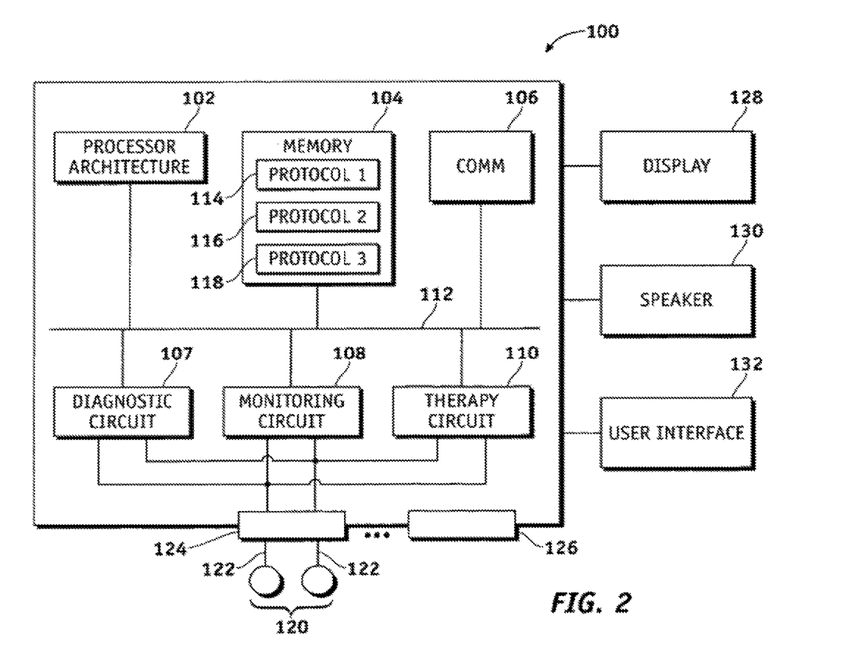
FIG. 2 is a schematic representation of an external defibrillator system configured in accordance with an example embodiment of the invention.

FIG. 2 is a schematic representation of a defibrillator 100 suitable for use with the resuscitation methodology as further described herein. Although not shown in FIG. 2, defibrillator 100 may include a number of functional elements, logical elements, and/or hardware components that support conventional defibrillator or monitoring features unrelated to the invention. Defibrillator 100 generally includes a processor architecture 102, a suitable amount of memory 104, a data communication element 106, a diagnostic circuit 107, a monitoring circuit 108, and a defibrillation therapy circuit 110. Defibrillator 100 may include a data bus 112 to facilitate communication of data or control signals between some or all of the above components.

The invention may be described herein with reference to symbolic representations of operations that may be performed by the various processing components. Such operations are sometimes referred to as being computer-executed, computerized, software-implemented, or computer-implemented. It will be appreciated that operations that are symbolically represented include the manipulation by the various microprocessor devices of electrical signals representing data bits at memory locations in the system memory, as well as other processing of signals. The memory locations where data bits are maintained are physical locations that have particular electrical, magnetic, optical, or organic properties corresponding to the data bits.

When implemented in software or firmware, various elements of the systems described herein (which may reside at a defibrillator device, a patient monitoring device, or the like) are essentially the code segments or instructions that perform the various tasks. The program or code segments can be stored in a processor-readable medium or transmitted by a computer data signal embodied in a carrier wave over a transmission medium or communication path. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links.

Processor architecture 102 may include at least one general purpose microprocessor, controller, or microcontroller that is suitably configured to control the operation of defibrillator 100. It should be appreciated that FIG. 2 depicts processor architecture 102 as a single distinct block for ease of description. In a practical embodiment, processor architecture 102 may be dispersed among a plurality of hardware components within defibrillator 100, and the processing logic associated with processor architecture 102 may actually be incorporated into other functional elements of defibrillator 100, such as diagnostic circuit 107, monitoring circuit 108, or therapy circuit 110.

Memory 104 may be realized as any processor-readable medium, including an electronic circuit, a semiconductor memory device, a ROM, a flash memory, an erasable ROM, a floppy diskette, a CD-ROM, an optical disk, a hard disk, an organic memory element, or the like. As described in more detail below, memory 104 is capable of storing instructions and data corresponding to different resuscitation protocols that may be recommended, initiated, or performed by defibrillator 100 during a resuscitation event. In this regard, FIG. 2 depicts a first resuscitation protocol 114, a second resuscitation protocol 116, and a third resuscitation protocol 118 stored in memory 104.

Communication element 106 is suitably configured to communicate with one or more devices as necessary to support the functionality described herein. For example, communication element 106 may be configured to support some or all of the following features (without limitation): communicate stored post-event data with a remote computing device; perform real-time communication of ongoing event data; facilitate transmission of instructions, data, and/or control signals between a patient monitoring device; or facilitate transmission of instructions, data, and/or control signals between devices that detect physiologic responses of the patient. It should be appreciated that communication element 106 may be optional in some deployments that utilize an AED for defibrillator 100. In a practical embodiment, communication element 106 may be configured to communicate with remote devices in accordance with at least one standardized data communication protocol (either wireless or wired). Such standardized data communication protocols include, without limitation: Bluetooth; IEEE 802.11 (any variation thereof); Ethernet; IEEE 1394 (Firewire); GPRS; USB; IEEE 802.15.4 (ZigBee); or IrDA (infrared). Communication element 106 may be realized with hardware, software, and/or firmware using known techniques and technologies. For example, defibrillator device 100 may include a wireless port configured to support wireless data communication with the remote device and/or a cable or wire port configured to support data communication, via a tangible link, with the remote device.

Alternatively (or additionally), post-event data may be transferred to a remote computing device using portable storage media. For example, the post-event data can be transferred or copied from memory 104 onto a portable storage device for transport to the remote computing device. The portable storage media may include, without limitation, a magnetic disk, a semiconductor memory device, a flash memory device, a floppy diskette, an optical disk (e.g., a CD or a DVD), a hard disk, or the like.

In operation, defibrillator 100 communicates with patient sensors 120 that may be attached to the patient undergoing treatment. In one practical embodiment, patient sensors 120 are attached to electrode leads 122 that are connected to defibrillator 100. In this regard, defibrillator 100 includes at least one connection port 124 configured to receive electrode leads 122. Alternatively, patient sensors 120 can be attached/connected directly to defibrillator 100. As depicted in FIG. 2, defibrillator 100 may include any number of additional connection ports 126 configured to receive leads, wires, cables, or wireless signals corresponding to additional sensors including, without limitation, accelerometers, acoustic transducers, oximeters, capnography sensors, blood-pressure recorders, contact sensors, optical sensors, magnetic sensors, or Doppler sensors. In a practical embodiment, patient sensors 120 may be realized as conventional defibrillation therapy electrode patches that are capable of monitoring patient data and delivering defibrillation pulses to the patient. For example, patient sensors 120 are preferably configured to detect the patient's ECG signal and the patient's chest impedance using techniques known to those skilled in the art (chest impedance is typically measured by applying a high frequency variable level carrier wave into the patient via patient sensors 118). As described in more detail below, defibrillator 100 can monitor the ECG signal, or a derivative of the ECG signal obtained by hardware or software manipulation of the ECG signal, to determine whether electrical cardiac response, such as electrical capture, has been obtained. In a practical embodiment, defibrillator 100 can concurrently sample the ECG and chest impedance signals during a resuscitation event, and monitor the patient for signs of mechanical cardiac response and electrical cardiac response at times when defibrillation therapy is not being administered. Although only two patient sensors 120 are depicted in FIG. 2, a practical embodiment may employ any number of patient sensors 120 defining any number of ECG leads (i.e., circuits), any number of patient sensors 120 defining any number of chest impedance measurement circuits, any number of patient sensors 120 for applying defibrillation pulses to the patient, and any number of patient sensors 120 configured to monitor, sense, or detect physiologic or other patient related data or signals that may be utilized during the resuscitation procedures as further described herein. For example, patient sensors 120 may include one or more pressure sensors, one or more accelerometers, one or more ultrasound sensors, or any number of conventional sensors, transducers, or detectors.

Therapy circuit 110 is generally responsible for the application of defibrillation pulses to the patient. Accordingly, therapy circuit 110 is coupled to connection port 124 to facilitate the delivery of defibrillation energy to patient sensors 120 via electrode leads 122. In an automated or automatic defibrillator, therapy circuit 110 may react to the determination of whether a defibrillation pulse is warranted and, if so, charge and discharge the defibrillation pulse circuit as needed. In this regard, therapy circuit 110 may be controlled by processor architecture 102 and, more specifically, by one of the stored resuscitation protocols 114/116/118. Therapy circuit 110 preferably operates in accordance with known defibrillation techniques and methodologies and such known aspects will not be described in detail herein.

Monitoring circuit 108 is suitably configured to receive the patient data or signals from patient sensors 120. As described above, such data may represent the patient ECG signal, the patient chest impedance signal, and/or other diagnostic signals. Monitoring circuit 108 may process the received data into a format for storage in memory 104, into a format for interpretation or further analysis by defibrillator 100, and/or into any suitable format. In practice, monitoring circuit 108 may perform analog to digital conversion on the received signals or otherwise condition the received signals for subsequent handling by defibrillator 100. In one practical embodiment of the invention, monitoring circuit 108 receives and analyzes a patient signal that is generated in response to a diagnostic signal administered by defibrillator 100, where such analysis determines whether electrical cardiac response and/or mechanical cardiac response has occurred. Monitoring circuit 108 may operate in accordance with known patient monitoring techniques and methodologies and such known aspects will not be described in detail herein.

Diagnostic circuit 107 is generally responsible for generating and administering diagnostic signals, and analyzing the patient reaction to such diagnostic signals to determine how best to proceed with the current resuscitation procedure. Briefly, diagnostic circuit 107 is configured to generate a suitable diagnostic signal having characteristics for eliciting a physiologic response from the patient. In particular, the diagnostic signal has certain power, waveform, and temporal characteristics designed to elicit mechanical cardiac response and/or electrical cardiac response from the patient. Diagnostic circuit 107 may also be suitably configured to analyze information obtained by defibrillator 100 in response to the diagnostic signals (such information may be received via patient sensors 120 and/or from a separate device connected to defibrillator 100). In the example embodiment, diagnostic circuit 107 determines whether one of the following conditions is present: mechanical cardiac response, such as mechanical capture; electrical cardiac response, such as electrical capture, in the absence of mechanical cardiac response; or absence of both mechanical and electrical cardiac response. Additionally, or alternatively, diagnostic circuit 107 can determine if the diagnostic signal has elicited any detectable patient reaction, whether or not such detectable reaction includes mechanical or electrical cardiac responses. Defibrillator 100 utilizes this determination to select an appropriate therapy protocol for the patient.

An alternate embodiment may utilize a non-electrical diagnostic signal in lieu of (or in addition to) an electrical diagnostic signal. For example, the non-electrical diagnostic signal may be one or more mechanically applied compressions, taps, or "thumps," administered to the patient manually or by automated equipment. As another example, the non-electrical diagnostic signal may be a mechanical vibration applied to the patient, or manual or mechanical manipulation of the patient's body. Defibrillator 100 can be suitably configured to monitor for physiologic responses (as described above) caused by such non-electrical diagnostic signals.

In accordance with one aspect of the invention, defibrillator 100 is suitably configured to generate and administer a stimulus signal that maintains mechanical and electrical capture of the patient's heart. In the example embodiment, the stimulus signal is applied to cause perfusion for a brief time period prior to the application of a defibrillation pulse. In practice, the stimulus signal has certain power, waveform, and temporal characteristics designed to maintain mechanical and electrical capture. Referring to FIG. 2, the stimulus signal may be generated and administered by diagnostic circuit 107 and/or by therapy circuit 110, depending upon the practical deployment of defibrillator 100.

Defibrillator 100 may also include a display element 128, at least one speaker 130, and a user interface 132. The specific configuration, operating characteristics, and functionality of display element 128, speaker 130, and user interface 132 can vary depending upon the practical implementation of defibrillator 100. For example, display element 128 may be a CRT, LCD, or plasma display, and user interface 132 may include buttons, a keypad, switches, and a pointing device such as a mouse or touchpad. Display element 128 is preferably configured to visually present various measured or calculated parameters of the patient and/or other information to the operator of defibrillator 100. For example, display element 128 can be configured to visually present the chest impedance, ECG, and/or other physiology signals of the patient. Display element 128 and/or speaker 130 may also be utilized to communicate instructions to the operator of defibrillator 100. Such instructions may be communicated before initiating the resuscitation procedure or during the resuscitation procedure. In practice, the instructions may correspond to the selected resuscitation protocol.

A patient monitoring device according to an example embodiment of the invention may be configured substantially as described above for defibrillator 100. In contrast to defibrillator 100, such a patient monitoring device need not include therapy circuit 110. In practice, such a patient monitoring device may be configured to perform the monitoring, diagnostic, and resuscitation protocol selection functions described herein, while operating in conjunction with a separate defibrillator device that provides the defibrillation therapy. For example, in addition to conventional patient monitoring operations, the patient monitoring device can administer a diagnostic signal, detect various physiologic responses, determine whether mechanical cardiac response or electrical cardiac response has occurred, identify an appropriate resuscitation protocol, and recommend or initiate that resuscitation protocol. The patient monitoring device may be configured to communicate control signals to a defibrillator device via a cable connection or a wireless data link. Alternatively, the patient monitoring device may be suitably configured to provide recommendations to a caregiver who, in turn, carries out the resuscitation protocol using the defibrillator device.

Figure 3:
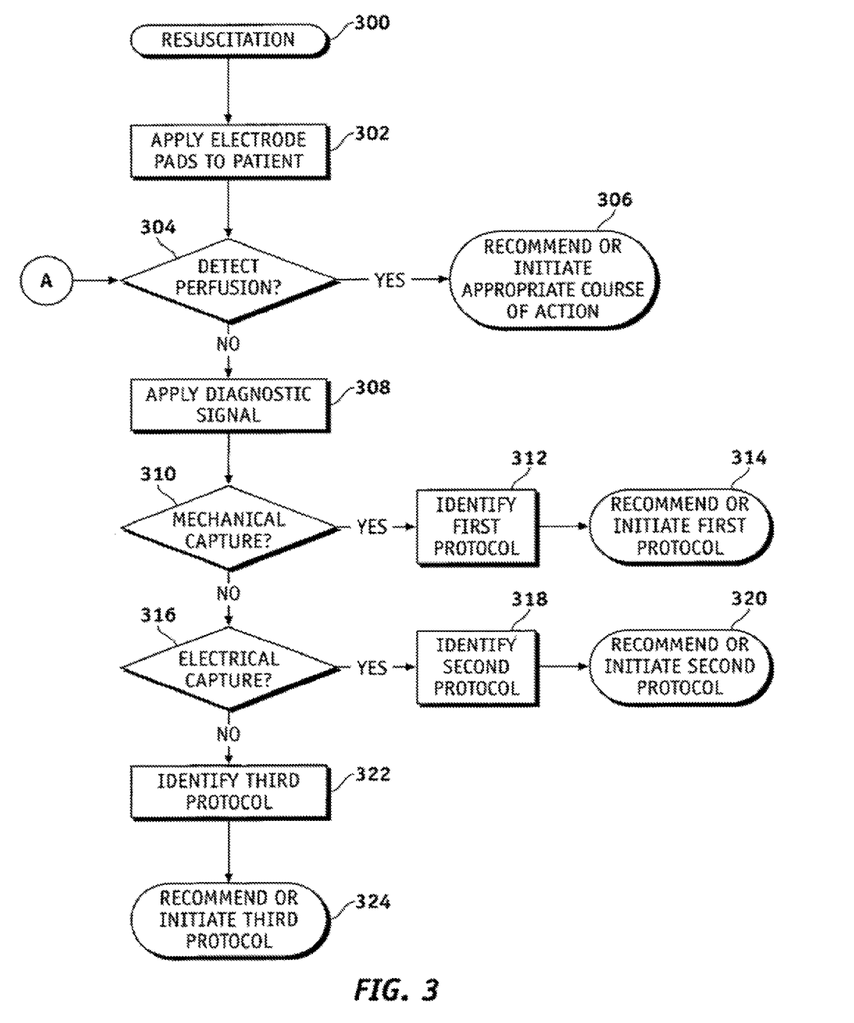
FIG. 3 is a flow diagram of a resuscitation process according to an example embodiment of the invention.

FIG. 3 is a flow diagram of a resuscitation process 300 according to an example embodiment of the invention. Process 300 or portions thereof may be performed by a defibrillator device, a monitoring device, a combination thereof, or any suitable system or apparatus configured as described herein. The various tasks performed in connection with process 300 may be performed by software, hardware, firmware, or any combination thereof. For illustrative purposes, the following description of process 300 may refer to elements mentioned above in connection with FIG. 1-2. In practical embodiments, portions of process 300 may be performed by different elements of a defibrillator or monitoring system, e.g., processor architecture 102, diagnostic circuit 107, monitoring circuit 108, or therapy circuit 110. It should be appreciated that process 300 may include any number of additional or alternative tasks, the tasks shown in FIG. 3 need not be performed in the illustrated order, and process 300 may be incorporated into a more comprehensive procedure or process having additional functionality not described in detail herein.

Resuscitation process 300 begins by applying the defibrillator electrode pads to the patient (task 302). In practice, a defibrillator device may have a setting or optional feature that allows the user to bypass the diagnostic procedure and proceed directly to defibrillation at any time after the electrode pads have been applied. Assuming that the diagnostic procedure is to be performed, the device may then be used to detect perfusion (query task 304). In practical embodiments, the device monitors the patient to determine whether a normal rhythm is present. Since a normal rhythm may not always be perfusing (pulseless electrical activity, for example), the device can check for a normal rhythm and further check for mechanical signs of circulation. If a pulse is detected with a normal rhythm, by either direct detection by the device or by the assessment of the rescuer, then the device may recommend or initiate an appropriate course of action (task 306). In this regard, the rescuer might be advised to monitor the patient, perhaps to wait for help to arrive before taking any further action, the rescuer might be advised to intervene as necessary to support the patient's airway, monitor breathing, peripheral pulse, patient responsiveness, blood/organ chemistry, or the like.

If a normal or perfusing rhythm is not detected, then the device generates and applies a suitable diagnostic signal to the patient (task 308). The diagnostic signal has characteristics for eliciting a physiologic response from the patient. In one practical embodiment, the diagnostic signal has characteristics for eliciting a cardiac response from the patient, e.g., electrical cardiac response and/or mechanical cardiac response. In the example embodiment, the diagnostic signal is a series of one or more electrical pulses applied via the electrode pads. In practice, the device may control one or more of the following characteristics of the diagnostic signal: average power; peak power; voltage; current; waveform shape (e.g., square, sinusoidal sawtooth, monophasic; biphasic; exponential); frequency; time period during which the diagnostic signal is applied; number of pulses applied; or the like. For example, the timing of the diagnostic signal pulses can be coupled to one or more of the monitored patient parameters. It should be appreciated that the magnitude of the diagnostic signal may need to be adjusted depending upon the current patient status. For example, the magnitude during VF may need to be higher than the magnitude during periods of slow rhythms (asystole, bradycardia, or sinus rhythm). In practice, diagnostic signals for slow rhythms may have currents in the range of twice the diastolic threshold (200 mA). On the other hand, diagnostic signals for fast rhythms such as VT or VF may require stronger electrical pulses, somewhere between the pacing threshold and the defibrillation threshold, depending on the responsiveness of the patient. The reaction to externally applied pulses by other skeletal muscles may also be interpreted. For example, if no reaction (i.e., muscle contraction) occurs, further resuscitation efforts may be discontinued.

The device may be suitably configured to apply a series of different diagnostic signals having different signal characteristics. In this regard, the signal characteristics can be manipulated in a controlled sequence to probe the responsiveness of the heart. In addition, the signal characteristics can be manipulated in an attempt to elicit a particular response from the heart. For example, if only electrical cardiac response is obtained from an initial diagnostic signal, a subsequent diagnostic signal may have a higher amplitude in an attempt to elicit an associated mechanical cardiac response, such as mechanical capture.

As mentioned above, the diagnostic signal is intended to elicit one of the following physiologic responses from the patient: mechanical cardiac response (such as mechanical capture); electrical cardiac response (such as electrical capture) in the absence of mechanical cardiac response; or absence of both mechanical and electrical cardiac response. The actual cardiac response will depend upon the current state or condition of the patient's heart, and will depend upon the amount of time that the heart has been without perfusion. In practical embodiments, the diagnostic signal may be configured to elicit one or more of the following physiologic responses: an electrical, mechanical, neurological, and/or chemical response that is related to the state of vital functions during resuscitation, for example, sub-threshold electrical polarization, local or global capture (electrical or mechanical or both), or wavefront generating (propagating or non-propagating).

Following application of the diagnostic signal, a current physiologic response is detected. In a practical AED implementation, the AED device analyzes signals, data, or information obtained from one or more sensors or detectors. Process 300 may utilize known techniques for the detection of mechanical cardiac response and electrical cardiac response, and the device may be suitably configured to accommodate such known techniques. For example, electrical capture and/or mechanical capture may be detected via the same electrode pads used for ECG monitoring and defibrillation therapy. Alternatively or additionally, the device may communicate with any number of other sensors/detectors configured to provide an indication of electrical and/or mechanical capture. If the device detects mechanical cardiac response, such as mechanical capture (query task 310), it may identify a first resuscitation protocol (task 312) that is specifically designed to treat patients that show perfusion in response to the diagnostic signal. In practice, the presence of mechanical cardiac response and electrical cardiac response may indicate a relatively high likelihood of defibrillation success. The device may also recommend or initiate the first resuscitation protocol (task 314). For example, in a fully automated implementation, task 314 may cause the device to carry out the initial steps or procedures set forth in the first resuscitation protocol. Alternatively (or additionally), the device may communicate a recommendation for the first resuscitation protocol to the caregiver using the display element, a speaker, or other user interface of the device, or communicate with adjunct devices through the communication port (for example, in a device that combines and integrates defibrillator and mechanical CPR functions). In practice, the first resuscitation protocol considers the likely response by the patient to defibrillation therapy. One resuscitation protocol suitable for use in this context is described in more detail below.

If the device does not detect mechanical cardiac response, but detects electrical cardiac response, such as electrical capture (query task 316), it may identify a second resuscitation protocol (task 318) that is specifically designed to treat patients that respond to the diagnostic signal with electrical cardiac response in the absence of mechanical cardiac response. In practice, the presence of electrical cardiac response in the absence of mechanical cardiac response may indicate a relatively intermediate likelihood of defibrillation success. The device may also recommend or initiate the second resuscitation protocol (task 320). For example, in a fully automated implementation, task 320 may cause the device to carry out the initial steps or procedures set forth in the second resuscitation protocol. Alternatively (or additionally), the device may communicate a recommendation for the second resuscitation protocol to the caregiver using the display element, a speaker, or other user interface of the device. In practice, the second resuscitation protocol considers the likely response by the patient to defibrillation therapy. One resuscitation protocol suitable for use in this context is described in more detail below.

If the device fails to detect either mechanical cardiac response or electrical cardiac response, it may identify a third resuscitation protocol (task 322) that is specifically designed to treat patients that respond to the diagnostic signal with the absence of both mechanical cardiac response and electrical cardiac response. In practice, the absence of both mechanical cardiac response and electrical cardiac response may indicate a relatively low likelihood of defibrillation success. The device may also recommend or initiate the third resuscitation protocol (task 324). For example, in a fully automated implementation, task 324 may cause the device to carry out the initial steps or procedures set forth in the third resuscitation protocol. Alternatively (or additionally), the device may communicate a recommendation for the third resuscitation protocol to the caregiver using the display element, a speaker, or other user interface of the device. In practice, the third resuscitation protocol considers the likely response by the patient to defibrillation therapy. One resuscitation protocol suitable for use in this context is described in more detail below.

Figure 4:
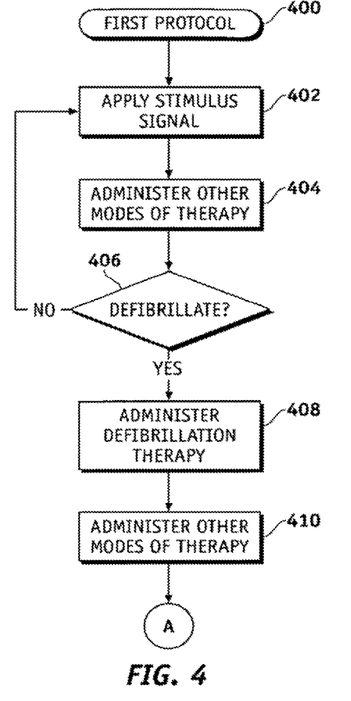
FIGS. 4-6 are flow diagrams of different resuscitation protocols suitable for use in connection with the resuscitation process shown in FIG. 3.

FIG. 4 is a flow diagram of a first resuscitation protocol 400 suitable for use in connection with resuscitation process 300. Protocol 400 or portions thereof may be performed by a defibrillator device, a monitoring device, a combination thereof, or any suitable system or apparatus configured as described herein. The various tasks performed in connection with protocol 400 may be performed by software, hardware, firmware, or any combination thereof. For illustrative purposes, the following description of protocol 400 may refer to elements mentioned above in connection with FIG. 1-2. In practical embodiments, portions of protocol 400 may be performed by different elements of a defibrillator or monitoring system, e.g., processor architecture 102, diagnostic circuit 107, monitoring circuit 108, or therapy circuit 110. It should be appreciated that protocol 400 may include any number of additional or alternative tasks, the tasks shown in FIG. 4 need not be performed in the illustrated order, and protocol 400 may be incorporated into a more comprehensive procedure or process having additional functionality not described in detail herein.

As mentioned above, first resuscitation protocol 400 is performed when the diagnostic signal elicits mechanical cardiac response and electrical cardiac response by the patient's heart. Protocol 400 may begin by applying a stimulus signal to the patient for a given period of time prior to defibrillation (task 402). The stimulus signal has characteristics for maintaining mechanical and electrical capture. In the example embodiment, the stimulus signal is a series of one or more electrical pulses applied via the electrode pads. In practice, the device may control one or more of the following characteristics of the stimulus signal: average power; peak power; waveform shape (e.g., square, sinusoidal sawtooth; monophasic; biphasic; exponential); frequency; time period during which the stimulus signal is applied; number of pulses applied; or the like. It should be appreciated that the stimulus signal may, but need not, correspond to the diagnostic signal. In other words, task 402 may be associated with the continued application of the diagnostic signal. The application of the stimulus signal may stimulate perfusion prior to defibrillation.

In addition to the stimulus signal, first protocol 400 may recommend or administer other modes of therapy (task 404) prior to defibrillation. For example, one or more of the following may be performed at this time: CPR; ventilation; drug therapy; pacing; post-extra systolic potentiation ("PESP"); or other electrical therapy. If protocol 400 determines that it is time to defibrillate the patient (query task 406), then the defibrillator device is controlled to administer defibrillation therapy to the patient (task 408). Following the defibrillation pulse, protocol 400 may recommend or administer other modes of therapy (task 410), such as: CPR; ventilation; drug therapy; pacing; PESP; or other electrical therapy. In a practical embodiment, resuscitation process 300 may be re-entered at query task 304 after the defibrillation pulse has been delivered. Consequently, the diagnostic techniques described above can be utilized before and/or after defibrillation therapy.

Figure 5:
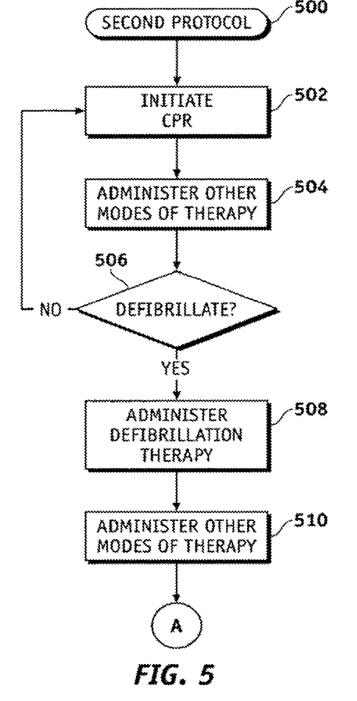

FIG. 5 is a flow diagram of a second resuscitation protocol 500 suitable for use in connection with resuscitation process 300. Protocol 500 or portions thereof may be performed by a defibrillator device, a monitoring device, a combination thereof, or any suitable system or apparatus configured as described herein. The various tasks performed in connection with protocol 500 may be performed by software, hardware, firmware, or any combination thereof. For illustrative purposes, the following description of protocol 500 may refer to elements mentioned above in connection with FIG. 1-2. In practical embodiments, portions of protocol 500 may be performed by different elements of a defibrillator or monitoring system, e.g., processor architecture 102, diagnostic circuit 107, monitoring circuit 108, or therapy circuit 110. It should be appreciated that protocol 500 may include any number of additional or alternative tasks, the tasks shown in FIG. 5 need not be performed in the illustrated order, and protocol 500 may be incorporated into a more comprehensive procedure or process having additional functionality not described in detail herein.

As mentioned above, second resuscitation protocol 500 is performed when the diagnostic signal elicits electrical cardiac response in the absence of mechanical cardiac response. Protocol 500 may also be performed if the first resuscitation protocol 400 was unsuccessful. Protocol 500 may begin by recommending or initiating CPR for the patient prior to defibrillation (task 502). As mentioned previously, CPR is desirable to stimulate perfusion for this type of patient because electrical stimulation alone does not result in perfusion. In practice, CPR can be performed by the caregiver or by a mechanical device.

In addition to CPR, second protocol 500 may recommend or administer other modes of therapy (task 504) prior to defibrillation. For example, one or more of the following may be performed at this time: CPR; ventilation; drug therapy; pacing; PESP; or other electrical therapy. If protocol 500 determines that it is time to defibrillate the patient (query task 506), then the defibrillator device is controlled to administer defibrillation therapy to the patient (task 508). Following the defibrillation pulse, protocol 500 may recommend or administer other modes of therapy (task 510), such as: CPR; ventilation; drug therapy; pacing; PESP; or other electrical therapy. In a practical embodiment, resuscitation process 300 may be re-entered at query task 304 after the defibrillation pulse has been delivered. Consequently, the diagnostic techniques described above can be utilized before and/or after defibrillation therapy.

Figure 6:
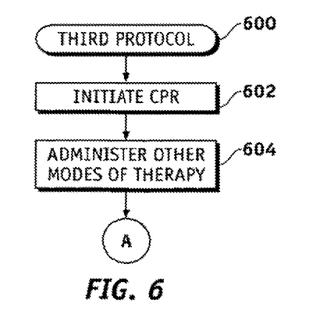

FIG. 6 is a flow diagram of a third resuscitation protocol 600 suitable for use in connection with resuscitation process 300. Protocol 600 or portions thereof may be performed by a defibrillator device, a monitoring device, a combination thereof, or any suitable system or apparatus configured as described herein. The various tasks performed in connection with protocol 600 may be performed by software, hardware, firmware, or any combination thereof. For illustrative purposes, the following description of protocol 600 may refer to elements mentioned above in connection with FIG. 1-2. In practical embodiments, portions of protocol 600 may be performed by different elements of a defibrillator or monitoring system, e.g., processor architecture 102, diagnostic circuit 107, monitoring circuit 108, or therapy circuit 110. It should be appreciated that protocol 600 may include any number of additional or alternative tasks, the tasks shown in FIG. 6 need not be performed in the illustrated order, and protocol 600 may be incorporated into a more comprehensive procedure or process having additional functionality not described in detail herein.

As mentioned above, third resuscitation protocol 600 is performed when the patient does not respond to the diagnostic signal, i.e., neither mechanical cardiac response nor electrical cardiac response is detected. Protocol 600 may begin by recommending or initiating CPR in lieu of immediate defibrillation (task 602). In situations where electrical cardiac response is not obtained, it might be better to administer CPR and possibly other modes of therapy (task 604) rather than spend valuable time performing defibrillation. In practice, CPR is performed by the caregiver. In addition to CPR, third protocol 600 may recommend or administer other modes of therapy (task 604) prior to defibrillation. For example, one or more of the following may be performed at this time: CPR; ventilation; drug therapy; pacing; PESP; or other electrical therapy. In a practical embodiment, resuscitation process 300 may be re-entered at query task 304 after an appropriate amount of CPR has been administered to the patient. Consequently, the diagnostic techniques described above can be utilized before and/or after defibrillation therapy.

Regardless of the resuscitation protocol followed, the diagnostic techniques described herein can be used to not only predict defibrillation therapy outcome, but also to prescribe post-defibrillation therapy such as CPR, drugs, or discontinued care. In this regard, a diagnostic signal applied externally following a defibrillation pulse can be used to determine the amount of subsequent CPR required. For example, if defibrillation results in a very slow rhythm and the diagnostic signal elicits electrical cardiac response without mechanical cardiac response, then further CPR may be recommended to facilitate revival of the patient. If, on the other hand, the post-defibrillation diagnostic signal elicits both electrical cardiac response and mechanical cardiac response, then additional CPR need not be performed and further patient assessment may be recommended.

The techniques described herein may also be utilized in conjunction with systems, applications, and technologies associated with transcutaneous pacing with auto-capture. For example, the diagnostic signal described herein may be applied as an initial signal by a transcutaneous pacing system, wherein the patient response to the diagnostic signal can be analyzed to determine one or more parameters or characteristics of the pacing signal. In this context, the diagnostic signal may be employed to determine a suitable amplitude and/or rate for the pacing signal.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A method of treating a patient, comprising:
   outputting a diagnostic stimulus signal to elicit a physiologic response from the patient, wherein the physiologic response comprises at least one of mechanical cardiac response, electrical cardiac response in the absence of mechanical cardiac response, or absence of both mechanical cardiac response and electrical cardiac response;
   detecting the elicited physiologic response;
   selecting one of a plurality of resuscitation protocols based upon the detected physiologic response, wherein at least one of the plurality of resuscitation protocols includes application of a defibrillation therapy, the selection based at least in part on a likely patient response to the defibrillation therapy; and
   initiating the selected resuscitation protocol,
   wherein, if the physiologic response is one of electrical cardiac response in the absence of mechanical cardiac response, initiating the selected resuscitation protocol includes initiating a protocol recommending drug therapy and outputting a recommendation to administer cardio pulmonary resuscitation (CPR) with the drug therapy.

2. The method of claim 1 wherein the electrical cardiac response in the absence of mechanical cardiac response is pulseless electrical activity.

3. The method of claim 1 wherein initiating the selected resuscitation protocol includes initiating a protocol recommending drug therapy for the patient and farther includes outputting the recommendation to administer CPR both before and after the drug therapy.

4. One or more tangible, non-transitory machine-readable storage media configured to store machine-executable instructions that, when executed by a processor of a system capable of treating a patient, cause the system to perform operations comprising:
   outputting a diagnostic stimulus signal to the patient to elicit a physiologic response from the patient, wherein the physiologic response includes at least one of mechanical cardiac response, electrical cardiac response in the absence of mechanical cardiac response, or absence of both mechanical cardiac response and electrical cardiac response;
   detecting the elicited physiologic response;
   selecting one of a plurality of resuscitation protocols based upon the detected physiologic response, wherein at least one of the plurality of resuscitation protocols includes application of a defibrillation therapy, the selection based at least in part on a likely patient response to the defibrillation therapy; and initiating the selected resuscitation protocol, wherein, if the physiologic response is one of electrical cardiac response in the absence of mechanical cardiac response, initiating the selected resuscitation protocol includes initiating a protocol recommending drug therapy for the patient and outputting a recommendation to administer cardio pulmonary resuscitation (CPR) in conjunction with the drug therapy.

5. The non-transient machine-readable storage media of claim 4 wherein the electrical cardiac response in the absence of mechanical cardiac response is pulseless electrical activity.

6. The non-transient machine-readable storage media of claim 4 wherein initiating the selected resuscitation protocol includes initiating a protocol recommending drug therapy for the patient and further includes outputting the recommendation to administer CPR both before and after the drug therapy.

7. An external defibrillator, comprising:
a connection port configured to receive a plurality of electrode leads for a patient;
a therapy circuit coupled to the connection port, the therapy circuit being configured to deliver defibrillation shocks and a diagnostic stimulus signal via the connection port; and
a processor configured to:
control the therapy circuit to generate and output the diagnostic stimulus signal to elicit a physiologic response from the patient, and in which the diagnostic stimulus signal is delivered to the patient via the connection port;
in response to the diagnostic stimulus signal, detect a physiological response from the patient that includes at least one of mechanical cardiac response, electrical cardiac response in the absence of mechanical cardiac response, or absence of both the mechanical cardiac response and the electrical cardiac response;
select one of a plurality of resuscitation protocols based upon the detected physiologic response, in which at least one of the plurality of resuscitation protocols includes application of a defibrillation therapy, the selection based at least in part on a likely response by the patient to the defibrillation therapy; and
initiate the selected resuscitation protocol, in which, if the physiologic response is electrical cardiac response in the absence of mechanical cardiac response, initiating the selected resuscitation protocol includes initiating a protocol recommending drug therapy for the patient and outputting a recommendation to administer cardio pulmonary resuscitation (CPR) with the drug therapy.

8. The external defibrillator of claim 7 wherein the electrical cardiac response in the absence of mechanical cardiac response is pulseless electrical activity.

9. The external defibrillator of claim 7 wherein initiating the selected resuscitation protocol includes initiating a protocol recommending drug therapy for the patient and further includes outputting the recommendation to administer CPR both before and after the drug therapy.

10. A method treating a patient, comprising:
applying a diagnostic stimulus signal to the patient to elicit a physiologic response from the patient, wherein the physiologic response comprises at least one of mechanical cardiac response, electrical cardiac response in the absence of mechanical cardiac response, or absence of both mechanical cardiac response and electrical cardiac response;
detecting the elicited physiologic response;
selecting one of a plurality of resuscitation protocols based upon the detected physiologic response, wherein at least one of the plurality of resuscitation protocols includes application of a defibrillation therapy, the selection based at least in part on a likely response by the patient to the defibrillation therapy; and
initiating the selected resuscitation protocol,
wherein, if the physiologic response is one of electrical cardiac response in the absence of mechanical cardiac response, initiating the selected resuscitation protocol includes initiating a protocol recommending initiating or continuing cardiopulmonary resuscitation (CPR) and administering drug therapy to the patient.

11. The method of claim 10 wherein the electrical cardiac response in the absence of mechanical cardiac response is pulseless electrical activity.

12. The method of claim 10 wherein initiating the selected resuscitation protocol further includes recommending an action related to the defibrillation therapy.

13. The method of claim 12 wherein recommending the action related to defibrillation therapy includes outputting a a recommendation to delay defibrillation therapy.

14. The method of claim 12 wherein recommending the action related to the defibrillation therapy outputting a recommendation to abort defibrillation therapy.

15. The method of claim 12 wherein recommending the action related to the defibrillation therapy includes outputting a recommendation to eliminate defibrillation therapy.

16. One or more tangible, non-transitory machine-readable storage media configured to store machine-executable instructions that, when executed by a processor of a system capable of treating a patient, cause the system to perform operations comprising:
applying a diagnostic stimulus signal to the patient to elicit a physiologic response from the patient, wherein the physiologic response includes at least one of mechanical cardiac response, electrical cardiac response in the absence of mechanical cardiac response, or absence of both mechanical cardiac response and electrical cardiac response;
detecting the elicited physiologic response;
selecting one of a plurality of resuscitation protocols based upon the detected physiologic response, wherein at least one of the plurality of resuscitation protocols includes application of a defibrillation therapy, the selection based at least in part on a likely response by the patient to the defibrillation therapy; and
initiating the selected resuscitation protocol,
wherein, if the physiologic response is one of electrical cardiac response in the absence of mechanical cardiac response, initiating the selected resuscitation protocol includes initiating a protocol recommending initiating or continuing cardiopulmonary resuscitation (CPR) and administering drug therapy to the patient.

17. The non-transient machine-readable storage media of claim 16 wherein the electrical cardiac response in the absence of mechanical cardiac response is pulseless electrical activity.

18. The non-transient machine-readable storage media of claim 16 wherein initiating the selected resuscitation protocol further includes recommending an action related to the defibrillation therapy.

19. The non-transient machine-readable storage media of claim 18 wherein recommending the action related to the defibrillation therapy includes outputting a recommendation to delay defibrillation therapy.

20. The non-transient machine-readable storage media of claim 18 wherein recommending the action related to the defibrillation therapy includes outputting a recommendation to abort defibrillation therapy.

21. The non-transient machine-readable storage media of claim 18 wherein recommending the action related to the defibrillation therapy includes outputting a recommendation to eliminate defibrillation therapy.

22. An external defibrillator, comprising:
a connection port configured to receive a plurality of electrode leads for a patient;
a therapy circuit coupled to the connection port, the therapy circuit configured to deliver defibrillation shocks and a diagnostic stimulus signal via the connection port; and
a processor configured to:
control the aid therapy circuit to generate the diagnostic stimulus signal to elicit a physiologic response from a heart of the patient, and in which the diagnostic stimulus signal is delivered to the patient via the connection port;
in response to the diagnostic stimulus signal, detect a physiological response that includes at least one of mechanical cardiac response, electrical cardiac response in the absence of mechanical cardiac response, and absence of both the mechanical cardiac response and the electrical cardiac response;
select one of a plurality of resuscitation protocols based upon the detected physiologic response, in which at least one of the plurality of resuscitation protocols includes application of a defibrillation therapy, the selection based at least in part on a likely response by the patient to the defibrillation therapy; and
initiate the selected resuscitation protocol, in which, if the physiologic response is electrical cardiac response in the absence of mechanical cardiac response, initiating the selected resuscitation protocol includes initiating a protocol recommending initiating or continuing cardiopulmonary resuscitation (CPR) and administering drug therapy to the patient.

23. The external defibrillator of claim 22 wherein the electrical cardiac response in the absence of mechanical cardiac response is pulseless electrical activity.

24. The external defibrillator of claim 22 wherein initiating the selected resuscitation protocol further includes recommending an action related to the defibrillation therapy.

25. The external defibrillator of claim 24 wherein recommending the action related to the defibrillation therapy includes outputting a recommendation to delay defibrillation therapy.

26. The external defibrillator of claim 24 wherein recommending the action related to the defibrillation therapy includes outputting a recommendation to abort defibrillation therapy.

27. The external defibrillator of claim 24 wherein recommending the action related to the defibrillation therapy includes outputting a recommendation to eliminate the defibrillation therapy.

* * * * *